United States Patent [19]

Ford

[11] Patent Number: 5,264,619
[45] Date of Patent: Nov. 23, 1993

[54] ANTI-ANDROGENIC CYCLO AND BICYCLO ALKENES

[75] Inventor: Larry C. Ford, Irvine, Calif.

[73] Assignee: Lafor Laboratories Limited, Newport Beach, Calif.

[21] Appl. No.: 4,972

[22] Filed: Jan. 15, 1993

[51] Int. Cl.⁵ .................... C07C 67/02; A61K 31/12; A61K 31/22
[52] U.S. Cl. ............................................. 560/256
[58] Field of Search ............... 560/256; 514/546, 691, 514/729

[56] References Cited

U.S. PATENT DOCUMENTS

| | | | |
|---|---|---|---|
| 4,535,182 | 8/1985 | Minai et al. | 560/256 X |
| 4,689,345 | 8/1987 | Kasha et al. | 514/546 |
| 4,822,823 | 4/1989 | Yamamoto et al. | 514/690 X |
| 4,963,583 | 10/1990 | Kunz | 514/546 X |
| 5,010,105 | 4/1991 | Lee | 560/256 X |
| 5,149,711 | 9/1992 | Hazato et al. | 514/546 X |

OTHER PUBLICATIONS

King, et al, "Increased Androgen Binding in Keloids and Its Inhibition with Cyoctol", *Recent Advances in Chemotherapy, Antimicrobial Section 1* 14th International Congress of Chemotherapy, Kyoto, 1985, pp. 259–260.

Ford, et al, "Dense Intraabdominal Adhesions: A Manifestation of Localized, Hyper-Androgen Receptors", *Recent Advances in Chemotherapy Antimicrobinal Sect. 1*, 14th International Congress of Chemotherapy, Kyoto, 1985, pp. 265–266.

Ford, et al., "Increased Androgen Binding in Keloids: A Preliminary Communication", *J. Dermatol. Surg. Oncol.*, 9:7 Jul. 1983, pp. 545–547.

Hammill, et al., "A Rat Model of Unilateral Utero-Tubo-Ovarian Abscess", *Reviews of Infectious Diseases*, vol. 6, Supplement, Mar.–Apr. 1984, pp. 896–900.

*Primary Examiner*—Arthur C. Prescott
*Attorney, Agent, or Firm*—Klein & Szekeres

[57] ABSTRACT

Compounds having the formula (i), (ii) and (iii),

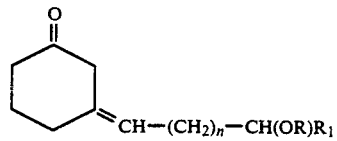
(i)

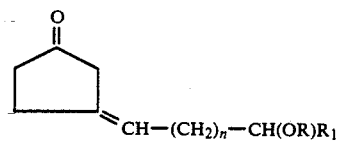

(ii)

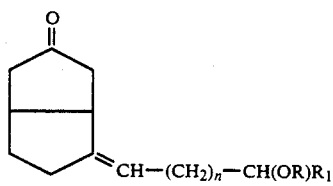

(iii)

where R is H, alkyl of 1 to 6 carbons, or $CO-R_2$ where $R_2$ is alkyl of 1 to 6 carbons; $R_1$ is H, $CH_3$, or $(CH_2)_m-CH_3$; n is an integer having the values of 2 to 10, m is an integer having the values of 1 to 6, have anti-androgen activity on secondary androgen receptor sites. The compounds are useful for treating mammals, including humans afflicted with acne, male pattern baldness, adhesions and keloids. The compounds are also effective for treating other diseases or conditions which are related to androgen receptors, such as undesirable formation of breast capsules in females after breast augmentation surgery, osteoarthritis and symptoms of Alzheimer's disease. The compounds also have inhibitory effect on the metabolism of certain microorganisms and fungi of the kind, the metabolism of which is normally known to be controllable by anti-androgen compounds.

38 Claims, No Drawings

ANTI-ANDROGENIC CYCLO AND BICYCLO ALKENES

BACKGROUND OF THE INVENTION

1. Field of the Invention

The present invention is in the field of new chemical compositions comprising cyclo and bicyclo alkenes which have anti-androgenic activity. The present invention is also in the field of pharmaceutical compositions having anti-androgenic activity, and methods of treating mammals, including humans for diseases and conditions where anti-androgenic drugs are beneficial. Moreover, the present invention is also in the field of controlling growth of microorganism and fungi with anti-androgenic agents.

2. Brief Description of the Prior Art

It has been known for a long time that androgens (male hormones) are implicated in the development of certain diseases and undesirable conditions such as male pattern baldness, acne, and formation of adhesions (particularly after abdominal surgery) and keloids. Moreover, androgens promote the growth of certain microbial organisms and fungi. Androgen antagonists, also known as anti-androgens, are compounds which block the receptor sites activated by androgens without bringing about an androgen like response on those receptor sites. It has been recognized in the prior art that androgen antagonists or anti-androgens can have a beneficial effect in either curing or alleviating the symptoms of the above-noted and related diseases and conditions.

Relatively recently, and with the increasing sophistication of the science of pharmachology, it has been recognized that there are at least two types (sub -types) of androgen receptors, and that for therapeutic purposes, it is desirable to selectively block only the so-called non-essential androgen receptors, which are implicated with the above-noted diseases or conditions (acne, male pattern baldness, keloids etc.). The present invention is directed to chemical compounds which have substantially selective antagonist effect only on these non-essential androgen receptors and are therefore useful for treating acne, male pattern baldness, adhesions and, keloids, etc., without having the undesirable anti-androgen effects (such as decrease in male libido or potency) of certain other anti-androgen drugs.

U.S. Pat. No. 4,689,345 (Kasha et al.) describes certain bicyclo alkanes which have anti-androgen effect and are useful for the treatment of acne, male pattern baldness, adhesions and keloids, and which also have inhibitory effect on the growth of certain microorganisms and fungi. The compounds described in U.S. Pat. No. 4,689,345 include a [3.2.0]heptan-7-one moiety and an alkyl moiety. Several of the in vitro and in vivo testing and assay procedures described in U.S. Pat. No. 4,689,345 are also applicable for testing or assaying the compounds of the present invention.

SUMMARY OF THE INVENTION

The present invention relates to new compounds having the formula (i), (ii) and (iii),

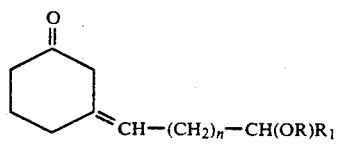

(i)

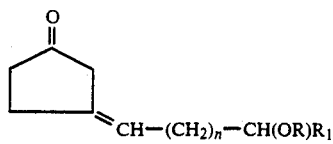

(ii)

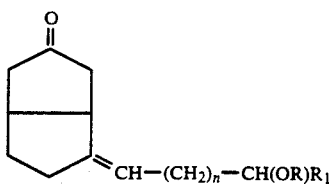

(iii)

where
R is H, alkyl of 1 to 6 carbons, or CO—$R_2$ where $R_2$ is alkyl of 1 to 6 carbons;
$R_1$ is H, $CH_3$, or $(CH_2)_m$—$CH_3$;
n is an integer having the values of 2 to 10, and
m is an integer having the values of 1 to 6.

The compounds of the invention have desirable anti-androgen activity in that the compounds are effective for treating mammals, including humans afflicted with acne, male pattern baldness, adhesions and keloids. The compounds are also effective for treating other diseases or conditions which are related to androgen receptors, such as undesirable formation of breast capsules in females after breast augmentation surgery, and symptoms of Alzheimer's disease. The compounds also have inhibitory effect on the metabolism of certain microorganisms and fungi of the kind, the metabolism of which is normally known to be controllable by anti-androgen compounds. Such microrganisms and fungi include a species of Fusarium which cause damage to agriculture, and pathogenic organisms such as Candida, Actinomyces, Norcardia, Cryptococcus, Torulopsis, Ascergillus and others. The compounds of the invention have the antagonist-like effect substantially selectively only on non-essential androgen receptors and therefore are substantially devoid of undesirable side effects (decrease of libido and male potency) of conventional anti-androgen drugs.

DETAILED DESCRIPTION OF THE INVENTION

General Embodiments

Chemical terms and names in the present description refer to and cover compounds falling within the definition that term or name as classically used in organic chemistry. The compounds of the present invention contain a double bond and therefore may have trans and cis (E and Z) isomers. In addition, the compound may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

The novel compounds of the present invention have the structures set forth in the SUMMARY OF THE INVENTION, and are shown by the formulas (i), (ii) and (iii).

Preferred compounds of the invention, with reference to the symbols used in formulas (i), (ii) and (iii), are those where R is H or lower alkyl, even more preferably where said lower alkyl group is OCH$_3$.

With reference to the symbol R$_1$, the preferred compounds of the invention are those where R$_1$ is H or CH$_2$CH$_3$. Further, preferred compounds of the invention are those where n is 3.

The most preferred compounds of the invention are shown below, as compounds I through XII.

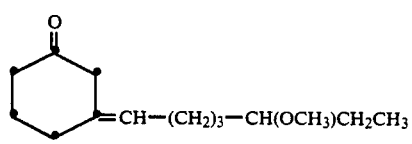
(Compound I)

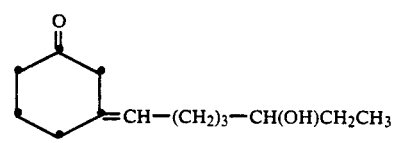
(Compound II)

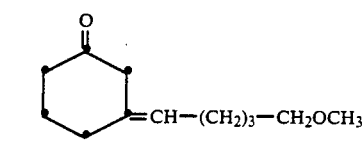
(Compound III)

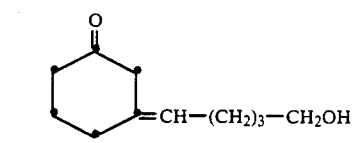
(Compound IV)

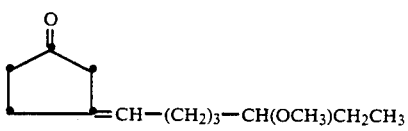
(Compound V)

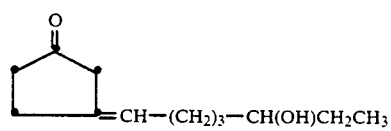
(Compound VI)

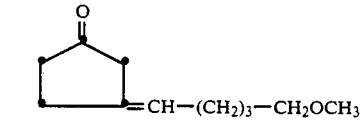
(Compound VII)

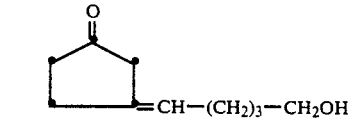
(Compound VIII)

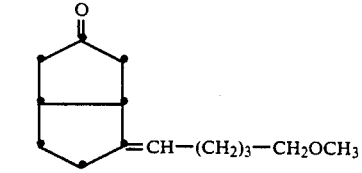
(Compound IX)

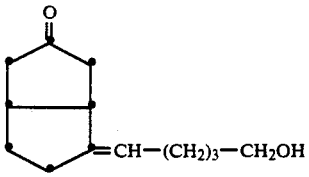
(Compound X)

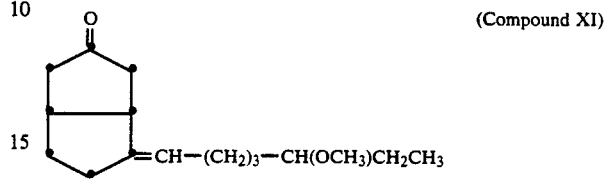
(Compound XI)

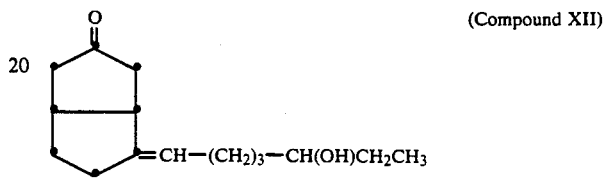
(Compound XII)

Synthetic Procedures for Obtaining the Compounds in Accordance with the Invention Generally speaking, the compounds of the invention which correspond to formula (i) are obtained as one of the products of the reaction between 3-(acetyloxy)-cyclohexanone and a triphenylphosphonium salt derived from triphenyl phosphine and a bromo or (chloro) alkoxy alkane.

Compounds of the invention which correspond to formula (ii) are obtained as one of the products of the reaction between 3-chlorocyclopentanone and a Grignard reagent derived from compounds having the general structure X—CH$_2$CH=CH(CH$_2$)$_n$—$_2$CH(OR)R$_1$ where X is halogen and the other symbols have the definition provided in connection with formula (ii).

Compounds of the invention which correspond to formula (iii) are obtained in accordance with Reaction Scheme 1. As it can be seen in the Reaction Scheme, spiro[bicyclo[3.3.0]octan-7,2'-[1,3]dioxolane-2-one (Compound XIII, a monoketal "derived" from bicyclo[3.3.0]octan-7,2'0-dione) is reacted with a Grignard reagent of Formula 2 where the symbols n and R are defined as in connection with formula (iii), and where "TBDMS" means t-butyldimethylsilyl. The resulting tertiary alcohol of Formula 3 is thereafter dehydrated by reaction with thionyl chloride in pyridine to provide a mixture of olefins of Formula 4. Deprotection in the form of removal of the ketal forming "ethylene glycol" moiety and of the t-butyldimethylsilyl group, by treatment with aqueous hydrogen fluoride provides the olefin mixture of Formula 5. Separation of this olefin mixture by chromatography yields compounds of formula (iii), where the R group, as defined in connection with (iii), is H. Acylated and alkylated derivatives, of the compounds where R is H can be obtained by conventional means, such as acylation with an acyl chloride, acyl anhydride, or alkylation with an alkyl halide.

Reaction Scheme I

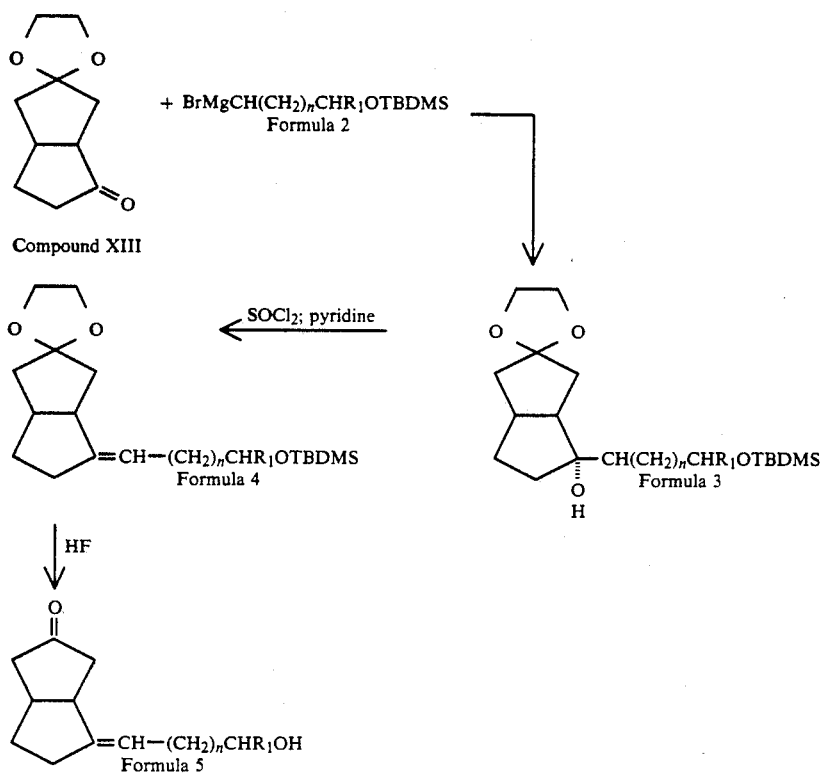

The starting material for Reaction Scheme 1, namely spiro[bicyclo[3.3.0]octan-7,2'-[1,3]dioxolane-2-one (Compound XIII) can be obtained in accordance with the sequence of reactions set forth in Reaction Scheme 2. In accordance with this scheme, ethyl 3-oxotricyclo[3.3.0.0$^{2,8}$]octan-2-ylcarboxylate (Compound XIV) is reacted with sulfuric acid in acetic acid to yield exo-6-acetobicyclo[3.3.0]octan-3-one (Compound XV). For Compound XIV see the published literature procedure of Callant et al. Tetrahedron 37, 2079-84 (1981), which is incorporated herein by reference. The ketone function of Compound XV is thereafter protected by forming a ketal with ethylene glycol, yielding Compound XVI. The acetyl function of Compound XVI is removed by treatment with base, and the resulting secondary alcohol (Compound XVII) is oxidized with pyridinium dichromate (PDC) to yield compound XIII. The oxidation with pyridinium dichromate is performed in accordance with the procedure of Corey et al., *Tet. Lett.*, 399-402 (1979), which is incorporated herein by reference.

Reaction Scheme 2

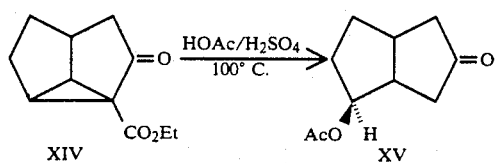

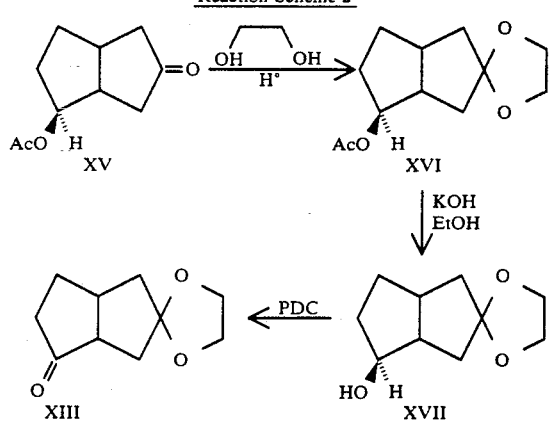

The preparation of the reagents which introduce the side chains into the compounds of the invention, namely the bromo or chloro alkoxy alkanes for the synthesis of compounds of formula (i), the compounds of the general structure X—CH$_2$CH=CH(CH$_2$)$_n$—$_2$CH(OR)R$_1$ for the synthesis of compounds of formula (ii), and the reagents of Formula 2 (See Reaction Scheme 1), can be prepared in accordance with synthetic methods disclosed in the literature and are available within the skill of the ordinary practicing synthetic organic chemist. By way of illustration, the following examples are provided.

1-Bromo-5-methoxyheptane (Compound XX) is a reagent used for preparing preferred compounds X and XX. Compound XX is prepared in accordance with Reaction Scheme 3, starting from commercially available 2-methyl-1,3-cyclohexanedione. Thus, with reference to Reaction Scheme 3, 2-methyl-1,3-cyclohexanedione is reacted with base (Ba(OH)$_2$) to yield 5-oxoheptanoic acid (Compound XXI). The oxo function of 5-oxoheptanoic acid (Compound XXI) is thereafter reduced, and the resulting hydroxy group, as well as the carboxylate function, are methylated to give methyl 5-methoxyheptanoate (Compound XXII). The carboxylate group of the latter is reduced (LiAlH$_4$) to give 5-methoxy-1-heptanol (Compound XXIII), which is thereafter reacted with carbontetrabromide to yield 1-bromo-5-methoxyheptane (compound XX).

sponding to formula (iii), and such reagents having a 5-carbon chain and a 7-carbon chain, respectively, are used for the synthesis of preferred compounds IX, X, XI and XII. These reagents can be obtained, within the skill of the practicing organic chemist, by reacting the appropriate 1-halogeno-hydroxy alkane with t-butyldimethylsilyl chloride. For example 1-(t-butyl,dimethylsilyloxy)-5-bromopentane or the corresponding 5-chloro compound (reagents used in the synthesis of preferred compounds IX and X) is made by reacting the corresponding primary alcohol with t-butyldimethylsilyl chloride.

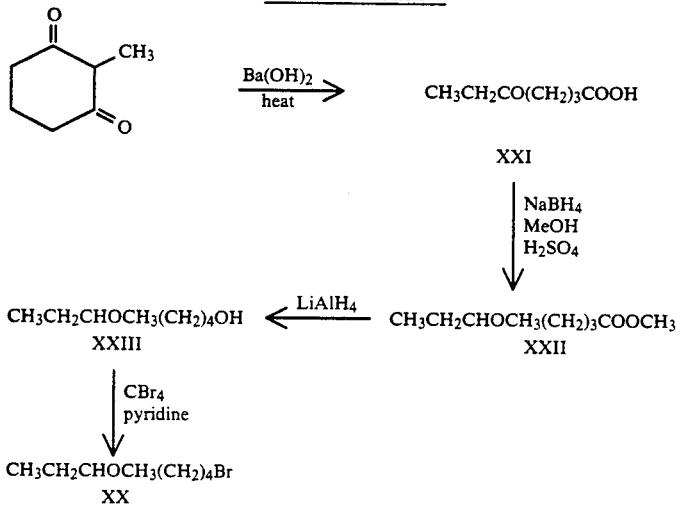

Reaction Scheme 3

1-bromo-5-methoxypentane (Compound XXX) is a reagent utilized for making prefered compounds III and IV. Compound XXX can be prepared from 5-bromo-1-pentanol (Compound XXXI). 5-bromo-1-pentanol (Compound XXXI) in turn, is obtained by hydrolysis of 5-bromopentanol-1-acetate (Compound XXXII), which itself is obtained from tetrahydropyran in accordance with the procedure described in U.S. Pat. No. 2,922,788 (Parcel), the specification of which is incorporated herein by reference.

1-Chloro-5-methoxy-2-heptene (Compound XL, boiling point 93°–95° C.) is a reagent utilized for the preparation of preferred compounds V and VI. Compound XL can be prepared within the skill of the practicing organic chemist from commercially available 5-hydroxy-1,4-heptadiene. The latter is methylated, for example with methyl bromide in the presence of strong base (sodium metal), and thereafter hydrogen chloride is added to saturate one double bond. Compound XL is the minor product of this addition, which is nevertheless isolable by distillation, or by other conventional techniques.

1-Chloro-5-methoxy-2-pentene (Compound L) is a reagent utilized for the preparation of preferred compounds VII and VIII. Compound L can be obtained from commercially available 5-hydroxy-1-pentyne by first reacting the latter with methylbromide in the presence of strong base (sodium metal), and thereafter adding one molecule of hydrogen chloride gas to the triple bond. The addition is accompanied by double bond migration, and Compound L is the minor but nevertheless isolable product (boiling point 82°–84° C.)

The reagents of Formula 2 (see Reaction Scheme 1) are utilized in the preparation of compounds corre-

BIOLOGICAL TEST RESULTS, CLINICAL TEST RESULTS

The beneficial anti-androgen activity of the compounds of the present invention can be confirmed by a number of tests, which are described in detail in U.S. Pat. No. 4,689,345. The specification of U.S. Pat. No. 4,689,345 is hereby expressly incorporated by reference. The results of tests and clinical data obtained with the novel compounds of the present invention are described below, together with a brief description of the nature of the disease, condition which is treated by the compound, and of the test in which the compounds have been applied.

Acne Vulgaris

Androgenic hormones are known to be causal in instigating the chain of effects which result in acne vulgaris as well as many other types of acne. The androgens stimulate the sebaccous glands to produce sebum which is then acted upon by bacteria ubiguitous in the population to produce free fatty acids which then act as mediators of inflammation. Several therapeutic modalities may be used at each of the above steps in the "acne cascade". For example, antibiotics, both topical and/or systemic can be used to decrease the amount of bacteria on the skin, desquammating agents such as benzoyl peroxide can be used to decrease oil content of the skin, or vitamin A analogs such as Retin A (Ortho) or Acutane (Hoffman LaRoche) can be used to decrease oil synthesis. A disadvantage of these prior art treatments, however, is that they work by poisioning fatty acid metabolism which can have very severe side effects on the skin, liver, and especially on a developing fetus.

In a test wherein inhibition of the binding of androgens to nuclear receptors is measured, sebaccous gland preparations were obtained from patients who underwent excision of acne lesions for cosmetic reasons, Compound II was found to block between 58-86 percent of the androgen receptors found in these isolated sebaccous gland preparations from patients with severe acne vulgaris.

Clinical Acne Vulgaris

In fifteen volunteers, ages 22-27, with a diagnosed history of severe acne vulgaris, all of whom had been seen by dermatologists, applied 0.5 mg of Compound I (dissolved in ethyl alcohol) twice a day to affected areas. In all of this study population, new acne lesions did not erupt after the second week of therapy and clearing with remission occurred after the third week of therapy.

Androgenic Alopecia

The loss or thinning of frontal hair in men has been reported to be universal with advancing age. In this genetically determined condition, the role of androgen metabolism has been more clearly established in male patients undergoing hair transplantations procedures. Research by the present inventor has demonstrated highly significant differences between the androgen receptor protein between balding, frontal tissues and hair bearing, occipital tissues.

Frontal (balding) tissues were examined for the effects of the subject antiandrogens.

Clinical Androgenic Alopecia

Compound I was applied to the balding (frontal) regions of ten (10) volunteers, ages 27-38, twice a day, 0.5 mg per application. The compound was applied in alcohol solution. In this population, as measured by using filter paper to occlude the drain, the hair loss was 75-177 hair per day. After six weeks of the above regimen, the loss was less than seven (7) per day. Terminal hair was visibly regrowing after ten weeks of applications and there were no side effects.

Androgenic Alopecia

In tissues samples obtained from balding frontal tissues of patients undergoing hair transplant operation, the following percent of Excess (non-essential) frontal receptor was blocked by the examplary compounds of this invention.

| Patient | Compound I *1:100 | Compound III *1:100 | Compound VII *1:100 | Compound XII *1:100 | CL *1:1000 |
|---|---|---|---|---|---|
| 1 | 88 | 80 | 71 | 49 | 68 |
| 2 | 95 | 81 | 69 | 46 | 20 |
| 3 | 90 | 80 | 72 | 50 | 69 |
| 4 | 95 | 82 | 68 | 55 | 75 |
| 5 | 95 | 84 | 59 | 52 | 72 |

*ratio of dihydro testosterone (DHT) to "antiandrogen" test compound.
CL = CYOCTOL ™

Biological Assays for Activity of Compounds (Nuclear receptors)

The nuclear receptors of androgens are very temperature labile. The tissues are chilled immediately to 0° C. unless being used as tissue culture explants, and then are immediately minced and placed in an appropriate tissue culture media. Radio labelled steriods are obtained from either New England Nuclear or Amersham. All other chemicals were of reagent grade obtained from commercial sources.

Nuclear receptors containing suspensions are added to $^3$H or $^{14}$C radiolabelled dihydrotestosterone (or other sex steriod) in order to achieve final concentrations of radiolabelled steriod of at least 2.0, 1.0, 0.6, 0.3, and 0.15 nM. It should be observed that other concentrations of steriods are some times used in various experiments. Also, when indicated, exogenous sex steriods are removed by prior treatment with 0.5% Dextran T-70-gelatin activated charcoal.

The radiolabelled steriod and the receptor preparations are reacted for an appropriate interval (1-24 hours), unbound radiolabelled steriod removed and an aliquot counted in a scintillation counter. Non-specific binding is determined at each concentration of radiolabeled steriod by adding a 200 fold excess of unlabelled steriod.

Specific receptor binding is then determined by the methods of Scatchard with the modification suggested by McGuire.

Anti androgenic activity is determined by adding the test compound at various final ratios to the radio labelled steriod, usually 0:1 to $10^4$:1, respectively.

Tissue Culture Assays for Anti androgen Activity

Tissue culture lines estabolished either from surgical explants or commercial sources are plated as the final "transfer" prior to experimentation into at least three 75 cm$^3$ flasks. The cells are removed and placed after counting into 36 well tissue culture tray, one 36 well tray for each concentration of steriod to be assayed. Non specific binding is determined by adding a 200 fold excess of unlabelled steriod. Anti androgen activity is determined by adding test compound to steriod at ratios of 0:1 to $10^4$:1, respectively. After incubation, radioactivity is determined by a scintillation counter.

Specific binding is determined as in the previous example. Further information relating to steriod binding assays can be obtained from the specification of U.S. Pat. No. 4,689,345 (incorporated herein by reference) and from the publications Scatchard, G. The Attraction of protein for small molecules and Ions Ann. N.Y. Acad. Sci. 81: 660-672, 1949; Chamness, G. C. and McGuire, W. L., Scatchard, plots: Common Errors in Correction and Interpretation Steriods 26(4): 538-542, 1975.

Anti-Fungal Activities

The inventor's earlier research, as well as that of several other investigators, have established the presence of sex steriod receptors in most fungal organisms.

Furthermore, the drugs that are presently clinically available against fungi, such as Amphotericin B, have very significant renal toxicities, as well as other organ side effects. Therefore, the compounds of the present invention which are capable of controlling fungal growth are valuable either alone or in combination with coventional antifungal compounds.

Anti-Fungal Clinical Studies

In 7 volunteers with chronic ($\geq$ 7 infections/yr) Candidia vaginitis, Compound I was absorbed on to clortrimizole (100 mg/suppository) for intra-vaginal use. All seven of these volunteers experienced culture and clinical cures compared to only 2/7 with culture and clinical cures with the same medication and regimen prior to entry to the study.

Anti-Fungal Testing (Cont)

It was found that production of mycotoxins by the Fuscarium species decreased by 79% as a result of addition of $1\times 10^{-3}$M of Compound II to the test media.

Contamination of grains with mycotoxins is the most significant cause of spoilage and wastage of grains world wide. These organisms, in particular the Fusarium species have significant levels of sex steriod binding proteins. Furthermore, some of these mycotoxins such as zearalone zearalenol are also estragenic, thus further emphasizing the role of sex steriods in these fungi.

In vitro Anti-Fungal Testing

The minimal fungalcidal concentration (MFC) of Amphotericin B againt *Cryptococcus neoformans* and *Cocciodes immitis* were reduced by more than two serial dilution tubes by the addition of $1\times 10^{-8}$M of Compound II. Similar reductions of MFC were seen with similar concentrations of compounds also against *Crypotococcus neoformans* and *Cocciodes immitis.*

Also, specific DHT binding was reduced at concentratios of DHT to anti androgen of 1:100 by 57 to 93% in isolates of the above organisms.

Clinical Skin Testing (Anti-wrinkling effect)

Ten volunteer, patients applied 0.1 mg/application of Compound I twice a day, to the lateral palpebral fissures. Prior to and at the termination of this ninety day study, dental impression polymer, after activation, was gently pressed against the study site. Scanning electron microscopy was performed and in all patients the "pore" size was decreased significantly and the surface area of the wrinkles were also reduced in all measurable areas by more than 40%.

Ten volunteer patients, aged 30-55 applied Compound I at 0.5 mg/application, twice a day to the suprapubic region. This area was selected because, in this population this skin area was not damaged by solar ultraviolet radiation. Also, this area is very active in androgen metabolism and has a high incidence of keloid formation. Prior to and at the termination of this study, patients underwent punch biopsies of this area. The tissues were stored at $-70°$ C. until analyzed for both elastin and collagen. In all the study patients, the amount of collagen was not effected, but of great significance was the de novo formation (synthesis) of elastin. As elastin synthesis normally ceases by age twenty-five, the present data demonstrate excellent clinical response to compounds of the invention.

Alzheimer's Diease (Clinical Efficacy)

The glial cell is thought to have many of the functions within the central nervous system (CNS) at the fibroblast in other parts of the body. Furthermore, the glial cell has been demonstrated in the inventor's research to have androgen receptors in the nucleus.

While the causes as well as much of the pathophysiology of Alzheimer's Disease is unknown, atrophy of the cerebral cortex and "scarring" of the glial cell has been established.

Five patient with stage I Alzheimer's disease were given orally 0.5 mg of Compound I twice a day. It was observed by the volunteer's families that by the second week of therapy, recognition, mobility, cognitave abilities, and physical activity improved in these patients and the patients regressed after the three month study period.

Treatment of Osteoarthritis

Twelve patients, ages 55-78 with a diagnosis of osteoarthritis were treated with one mg. of compound 1 once daily. The test material was applied to the skin surrounding either the wrists, knees, or hands. In the case of the wrist or knee application, the skin was occluded with a polymer, elastic dressing or in the case of the hands, occlusive polymer gloves. The skin was occluded for one hour then the occlusive dressings were removed. At the fourth to seventh day, all patients noted markedly decreased pain and by the fourteenth day, all patients had increased mobility. Additionally, all patients were able to reduce their dosage of nonsteroidal anti-inflammatory drugs.

Inhibition of Breast Capsule Formation

Breast capsules formation following surgery for mammary augmentation for either reconstructive or cosmetic indications is the most significant and potentially disfiguring complication of these surgeries. Such capsules form in 5-90% of the patients. In the inventor's earlier research, this problem was viewed as a subdermal keloid because of the histopathological appearance and very high concentrations of non-essential androgen receptor proteins in the capsule tissue. For the present tests surgical explants were obtained from patients undergoing surgical excession of the breast capsules for appropriate surgical indications. These explants were established in tissue culture.

Breast Capsules (Clinical Efficacy)

In 5 volunteers who had previously undergone mammary augmentation and subsequently developed deforming capsules formation bilaterally, Compound I was applied topically in alcohol solution at 0.1% concentration, twice a daily. In all patients, at the end of thirty days, the capsules decreased in mass so much that gentle pressure allowed their disruption. The patients continued to apply the compound for an additional 60 days with no further recapsulation.

| Percent of excess (non-essential) androgen receptors blocked. | | | | | |
|---|---|---|---|---|---|
| Patient # | Compound #I 1:100 | Compound #IV 1:100 | Compound #VIII 1:100 | Compound #IX 1:100 | CL 1:1000 |
| Breast Capsules Fibroblasts - Tissue Culture | | | | | |
| 1 | 86 | 76 | 69 | 46 | 77 |
| 2 | 90 | 79 | 60 | 49 | 64 |
| 3 | 95 | 81 | 58 | 44 | 78 |
| 4 | 96 | 82 | 59 | 44 | 81 |
| 5 | 89 | 70 | 62 | 51 | 61 |
| Whole Cells | | | | | |
| 1 | 86 | 72 | 62 | 42 | 66 |
| 2 | 89 | 73 | 60 | 46 | 71 |
| 3 | 79 | 64 | 57 | 49 | 55 |
| 4 | 87 | 76 | 49 | 51 | 73 |
| 5 | 78 | 49 | 53 | 50 | 48 |

CL = CYOCTOL ™

Keloids are among the most common disorders of healing of wounds and among the earliest described conditions of the skin being described in the Smith papyrus dating to 2500 B.C. The role of the sex hormones in keloids has been observed by several investigations, but it was the present inventor's research that identified the markedly elevated levels of androgen receptors in these tissues.

The effects of the compounds of the invention were assayed in surgical explants of keloids as well as in homogenates from whole keloid tissues. The surgical explants were obtained aseptically from patients undergoing surgical removal of their keloid(s). The explants were established in tissue according to standard methods.

The compounds were assigned at a final combination of DHT to compound of 1:4, 1:10, 1:100 1:1000, 1:10,000, respectively.

The compounds blocked the DHT receptor protein only in the non essential receptor, and not in the essential receptor even in doses of $10^4$ to one.

In the whole tissue preparations, very similar results were obtained.

| Percent of excess (non-essential) androgen receptor blocked | | | | | |
|---|---|---|---|---|---|
| Patient # | Compound #I 1:100 | Compound #II 1:100 | Compound #III 1:100 | Compound #IX 1:100 | CL 1:1000 |
| Keloids | | | | | |
| 1 | 98 | 88 | 72 | 33 | 80 |
| 2 | 95 | 88 | 66 | 39 | 83 |
| 3 | 98 | 81 | 68 | 46 | 79 |
| 4 | 90 | 74 | 69 | 35 | 68 |
| 5 | 98 | 82 | 72 | 41 | 81 |
| Keloids (Fibroblasts) | | | | | |
| 1 | 95 | 87 | 79 | 46 | 77 |
| 2 | 95 | 85 | 70 | 51 | 72 |
| 3 | 95 | 80 | 69 | 49 | 68 |
| 4 | 97 | 82 | 70 | 51 | 84 |
| 5 | 98 | 83 | 72 | 39 | 78 |

CL = CYOCTOL ™

Clinical Keloids

Compound I was injected intralesionally into volunteers with keloids at a dose of 0.2 mg/cm$^3$ of estimated keloid volume. In 3/5 patients, the keloid regressed completely after the second dose given 1 week after the first dose. The remaining (2/5) patients' keloids completely regressed after the third intra lesional injection.

Compound I was suspended in base as applied twice a day to the keloids of 5 volunteers at a concentration of 0.01%. A fifty percent decrease in the keloids were seen at 40–60 days and regression to a normal cistothrix at 150–180 days. This type of application was significantly slower than the intra lesional injections.

Biological Assays of Adhesions

The most common cause of involuntary sterility in human females is the sequlae of chronic pelvic inflammatory disease. Furthermore, the most common and significant cause of long term surgical complications is also dense adhesions which in the above examples have a very similar histopathogical appearance.

These dense adhesions are not unlike the dense banks of collagens and fibroblasts seen in the histopathogical appearance of keloid or hypertroplice scar tissues. Furthermore, as with keloids, these dense adhesions have elevated levels of androgen receptor proteins, with "normal" levels of both estrogen and progesterose receptor.

The effects of these anti-androgen compounds of the present invention on these abnormal tissues were assayed both in vivo and in vitro.

The tubo-ovaran abcess model of Hammill et al. A Rat Model of Unilateral Utero-Tubo-Ovarian Abscess, REVIEWS OF INFECTIOUS DISEASES, Vol. 6, Supplement 1–5, March–April 1984 was used to access the effects of these compounds on adhesion formation in the rat. Briefly, this model uses anaerobic and aerobic bacteria to form an abcess which stimulates very closely the human clinical stimulation.

The rats were given Primaxin (MSD) intra veinously and the compound of the invention intrapertionally. Animals were sacrificed at twelve (12) weeks and the resultant scarring scored according to the Gainsville method of grading the stage of pelvic inflammatory disease. It should be observed that these compounds do not have antibacterial activity at these doses and therefore the Primaxin (MSD) was essential to prevent the animals dying of septic shock. Furthermore, it should be observed that Primaxin( MSD) is FDA approved for this clinical indication.

As is evident, the compounds of the invention were highly effective in preventing adhesions in this tubo-ovarian abcess model.

| | Adhesions Rat Model | |
|---|---|---|
| Grade of Adhesions | Primaxin (MSD) | Primixin + Compound I |
| | IV, n = 8 | O, n = 8 |
| | III, n = 2 | I, n = 2 |

Surgical Adhesions in Humans

Clinically significant dense adhesions were obtained from patients undergoing gynecological surgery with the diagnosis of a prior history of pelvic inflammatory disease for gynecological indications. These surgical explants were cultured according to the methods above.

As is very evident, all the test compounds worked at ratios which could be readily and easily achieved clinically.

Surgical explants of clinically dense intra abdominal adhesions were obtained from general surgical patients with the diagnosis of complications secondary to these adhesions.

| Percent of excess (non-essential) androgen reactor blocked | | | | | |
|---|---|---|---|---|---|
| Patient # | Compound #I 1:100 | Compound #II 1:100 | Compound #VI 1:100 | Compound #IX 1:100 | Cl 1:1000 |
| 1 | 88 | 72 | 58 | 37 | 70 |
| 2 | 86 | 74 | 57 | 41 | 70 |
| 3 | 88 | 79 | 59 | 46 | 69 |
| 4 | 91 | 75 | 62 | 49 | 74 |
| 5 | 78 | 69 | 60 | 35 | 51 |
| Adhesions (fibroblasts) | | | | | |
| 1 | 77 | 70 | 69 | 56 | 43 |
| 2 | 89 | 75 | 41 | 42 | 66 |
| 3 | 87 | 80 | 60 | 41 | 59 |
| 4 | 85 | 79 | 55 | 55 | 86 |
| 5 | 79 | 80 | 59 | 53 | 42 |

CL = CYOCTOL ™

FORMULATIONS, METHODS OF ADMINISTRATION

The above-described clinical tests have provided examples for administration of the compounds of the present invention. Generally speaking, depending on the disease or condition to be treated or alleviated, the compounds of the invention may be delivered topically or systemically, in such pharmaceutical compositions which are commonly used in the art for the desired delivery. Specifically, shampoos, ointments and sustained release transdermal compositions can be used for topical delivery of the compounds of the invention. Shampoos are particularly advantageous for treatment of male pattern baldness. Systemic delivery of the compounds of the invention can be through oral dosage units, such as tablets, capsules and liquid oral dosage units. Sublingual administration and administration through rectal suppositories is also feasible, as well as administration by injection. Control of fermentation processes with the compounds of the invention may be affected by adding the applicable compound to the ferementation process in a suitable solvent, such as ethanol.

Generally speaking treatment of any disease or condition in mammals, including human patients, will be effected by administration of the therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that for a normal adult a dosage of 0.0001 to about 40 mg per oral dosage unit form of the active compound will be used for systemic delivery, and preferably the oral dosage will be from about 0.01 mg to about 2 mg per oral dosage unit form. For topical (transdermal) applications it is anticipated that the pharmaceutical composition (such as ointment, cream, solution etc.) will contain a concentration of 0.001 to 5 % by weight of the active compound of the invention. A more preferred range of concentration is from about 0.05 to about 3 % by weight.

For still further descriptions of routes and modes of administration, and methods of treatment, reference is made to the specification of U.S. Pat. No. 4,689,345 (incorporated herein by reference).

SPECIFIC EXAMPLES

5-Oxoheptanoic acid (Compound XXI)

A modification of the procedure of Ijima et al. Chem. Pharm. Bull. 19, 1053-5 (1971) was used. A solution of 2-methyl-1,3-cyclohexanedione (40 g, 0.317 mole, Aldrich) and Ba(OH)$_2$.8H$_2$O (360 g) in water (840 mL) was heated at reflux for 48 h. After standing overnight at room temperature and cooling to 0° C., the precipitated barium hydroxide was removed by suction filtration. CO$_2$ gas (generated from Dry Ice) was bubbled through the filtrate to precipitate any remaining barium hydroxide as barium carbonate. The precipitate was removed by suction filtration, and water was removed in vacuum until crystallization started. The resulting mixture was acidified to pH 1 (conc. HCl) and extracted with OEt$_2$ (3×300 mL). The extract was dried (Na$_2$SO$_4$) and stripped of solvent in vacuum giving 5-oxoheptanoic acid (Compound XXI) as a white solid (43.3-45.1 g, 95-99%, lit.[112] 69%): mp 48°-49.5° C. (lit.[182] 50° C.); IR (KBr pellet) cm$^{-1}$ 3000 (very br), 1725, 1710, 1690, 1460, 1435, 1420, 1380, 1340, 1280, 1210, 1120, 1085, 985, 910, 770, 685; $^1$H NMR (200 MHz, CDCl$_3$) δ 10.2 (br, 1H), 2.51 (t, 7.1 Hz, 2H), 2.43 (q, 7.3 Hz, 2H), 2.40 (t, 7.1 Hz, 2H), 1.91 (rough pentet, 2H), 1.06 (t, 7.3 Hz, 3H); $^{13}$C NMR (22.5 MHz, CDCl$_3$) δ 211.5, 178.6, 41.0, 36.0, 33.1, 18.7, 7.8; mass spectrum (16 eV) m/e (% base) 144 (M+, 4.1), 126 (61.3), 115 (88.8), 98 (40.0), 87 (40.1), 70 (21.3), 57 (100); TLC (OEt$_2$, I$_2$) Rf=0.37.

Methyl 5-methoxyheptanoate (Compound XXII)

5-Oxoheptanoic acid (compound XXI) was reduced using a modification of the procedure reported by Ijima et al. supra. NaBH$_4$ (10 g, 0.26 mole) was added in portions to a stirred solution of 5-oxoheptanoic acid (Compound XXI, 28.8 g, 0.20 mole) in 10% aqueous NaOH (200 mL, 0.50 mole) so that the temperature never exceeded 55° C. The reaction was stirred at 40° C. for 12 h and then cooled to 0° C. Concentrated HCl was added slowly (vigorous reaction at first) to pH 1. The stirred reaction was allowed to come to room temperature and then heated briefly to 90° C. After slow cooling, the resulting 2-phase mixture was extracted with OEt$_2$ (4×250 mL). The extract was dried (Na$_2$SO$_4$). Removal of the OEt$_2$ gave 30.3-31.5 g of a yellowish oil containing a small amount of suspended solid. The mixture, consisting mainly of 5-hydroxyheptanoic acid (57) and 6-ethyl-tetrahydro-2H-pyran-2-one (56), was used without further purification. (The ratio of acid to lactone is usually about 2:3 as seen by integration of the methine protons of each molecule. The methine proton resonance for the acid is centered at 3.6 ppm and the methine of the lactone is at 4.2 ppm. When the mixture is distilled, water is collected and then pure lactone, bp 55°-7° C. (0.2 mm), (lit.[112] bp 102°-10° C. (5 mm)); IR matches literature;[112] $^1$H NMR (60 MHz, CDCl$_3$) δ 3.95-4.45 (m, 1H), 2.2-2.9 (m, 2H), 1.3-2.2 (complex, 6H), 1.0 (t, 7 Hz, 3H).)

The mixture was combined with absolute MeOH (300 mL), HC(OMe)$_3$ (400 mL), and H$_2$SO$_4$ (10 mL), stirred 2-3 days at room temperature, poured into sat. aqueous NaHCO$_3$ (2 L), and extracted with OEt$_2$ (3×300 mL). The extract was washed (250 mL sat. NaHCO$_3$; 100 mL brine) and dried (Na$_2$SO$_4$). Removal of the solvent gave a slightly yellow oil (32-46 g). Distillation gave a forerun, bp 35° C. (52 mm) and then methyl 5-methoxyheptanoate (Compound XXII, 27.2-30.7 g, 78-88%) as a colorless oil: bp 117° C. (36 mm); IR (film) cm$^{-1}$ 2960, 2940, 2880, 2825, 1745, 1465, 1440, 1380, 1370, 1250, 1200, 1170, 1130, 1095, 1030, 1010, 990, 925, 885, 830; $^1$H NMR (200 MHz, CDCl$_3$) δ 3.67 (s, 3H), 3.32 (s, 3H), 3.10 (rough pentet, 1H), 2.33 (t, 7.4 Hz, 2H), 1.4-1.85 (complex, 6H), 0.89 (t, 7.4 Hz, 3H); $^{13}$C NMR (22.5 MHz, CDCl$_3$) δ 174.1, 81.7, 56.4, 51.5, 34.2, 32.4, 25.8, 20.9, 9.3; mass spectrum (70 eV) m/e (% base) 174 (M+, not observed), 159 (1.4), 145 (25.2), 113 (38.6), 111 (10.9), 83 (13.1), 74 (12.7), 73 (100), 71 (93.3); high resolution mass spectrum (70 eV) m/e 159.1035 (M+ - CH$_3$CH$_2$., calculated 159.10215 for C$_8$H$_{15}$O$_3$), 145.0852 (M+ - CH$_3$CH$_2$., calculated 145.0865 for C$_7$H$_{13}$O$_3$). TLC (OEt$_2$, vanillin dip) R$_f$=0.60.

5-Methoxy-1-heptanol (Compound XXIII)

A stirred suspension of LiAlH$_4$ (15.2 g, 0.40 mole) in dry OEt$_2$ (700 mL) was cooled to 0° C. Methyl 5-methoxyheptanoate (Compound XXII, 34.8 g, 0.20 mole) in dry OEt$_2$ (100 mL) was added dropwise over $\frac{1}{2}$ h. The reaction was allowed to slowly warm to room temperature and stirred for an additional 12 h. The excess hydride was destroyed by dropwise addition of sat. aqueous Na$_2$SO$_4$ (extremely vigorous reaction) to the rapidly stirred reaction mixture until the gray color was completely destroyed and only a snow white precipitate remained (further addition of sat. Na$_2$SO$_4$ increased the water content of the product and necessitated drying before the next reaction). The precipitate was filtered and washed with dry OEt$_2$ (5×300 mL). Removal of the ether gave 5-methoxy-1-heptanol (Compound XXIII, 29.2 g, 100%) as a colorless oil, sufficiently pure for further reactions: IR (film) cm$^{-1}$ 3390, 2970, 2945, 2875, 2830, 1465, 1440, 1380, 1200, 1170, 1135, 1094, 1060, 1040, 918; $^1$H NMR (200 MHz, CDCl$_3$) δ 3.66 (m, 2H), 3.33 (s, 3H), 3.10 (rough pentet, 1H), 1.74 (s, 1H), 1.3–1.7 (complex, 8H), 0.89 (t, 7.4 Hz, 3); $^{13}$C NMR (22.5 MHz, CDCl$_3$) δ 82.2, 62.4, 56.4, 32.8, 32.8, 25.8, 21.6, 9.4; high resolution mass spectrum (70 eV) m/e 146 (M$^+$, not observed), 117.0918 (M$^+$ - CH$_3$CH$_2$., calculated 117.0916 for C$_6$H$_{13}$O$_2$); TLC (OEt$_2$, vanillin dip) R$_f$=0.30.

1-Bromo-5-methoxyheptane (Compound XX)

A solution of 5-methoxy-1-heptanol (Compound XXIII, 27.7 g, 0.19 mole), CBr$_4$ (116.7 g, 0.38 mole), pyridine (15.4 mL, 0.19 mole), and dry OEt$_2$ (750 mL) was stirred mechanically under an inert atmosphere and cooled to 0° C. PPh$_3$ (105 g, 0.40 mole) dissolved in OEt$_2$ (500 mL) was added dropwise over 5 h. stirring was continued at 0° C. for 4 h and then at room temperature overnight. The solvent was removed in vacuum at 0° C. giving a pinkish solid which was extracted with pentane (4×500 mL). Similar removal of the pentane gave a yellowish oil (65 g) with a small amount of suspended solid. Bromoform and remaining PPh$_3$ and OPPh$_3$ were removed by column chromatography (11 g portions 3× each on 2 300 g silica gel columns, eluted with 4:1 (v/v) hexane-OEt$_2$). Distillation gave 1-bromo-5-methoxyheptane (31.7 g, 80%) as a colorless oil: bp 45°–7° C. (15 mm); $^1$H NMR (200 MHz, CDCl$_3$) δ 3.42 (t, 6.7 Hz, 2H), 3.33 (s, 3H), 3.09 (m, 1H), 1.88 (m, 2H), 1.4–1.6 (complex, 6H), 0.89 (t, 7.4 Hz, 3H); $^{13}$C NMR (22.5 MHz, CDCl$_3$) δ 81.8, 56.5, 33.6, 33.2 32.3, 25.9, 24.2, 9.4.

5-Bromopentanol-1-acetate (Compound XXXII)

The procedure of U.S. Pat. No. 2,922,788 was used. Acetyl bromide (420 g, 3.4 mole) was combined with zinc (30 mesh, 3 g, 0.045 mole) and warmed to about 60° C. for 30 min with constant stirring. Tetrahydropyran (275 g, 3.2 mole) was added dropwise over 2 h. The reaction was cooled periodically during the addition period to keep the temperature between 60° and 70° C. The temperature was raised to 90° C. for 30 min, cooled, and then diluted with CH$_2$Cl$_2$ (500 mL). Ice was added (200 g) and the reaction was shaken vigorously for several minutes The organic layer was washed (2×200 mL sat. NaHCO$_3$; 200 mL brine), dried (MgSO$_4$), and stripped of solvent in vacuum. Fractional distillation gave a nearly colorless oil (602.2 g, 90%): bp 120°–1° C. (19 mm) (lit.[121] 109°–11° C. (14 mm)); IR (film) cm$^{-1}$ 2950, 2900, 2870, 1740, 1465, 1460, 1435, 1395, 1370, 1245 (broad), 1045, 735; $^1$H NMR (200 MHz, CDCl$_3$) δ 4.08 (t, 6.3 Hz, 2H), 3.42 (t, 6.7 Hz, 2H), 2.06 (s, 3H), 1.09 (pentet, 7 Hz, 2H), 1.4–1.77 (m, 4H); $^{13}$C NMR (22.5 MHz, CDCl$_3$) δ 170.9, 64.0, 33.4, 32.3, 27.8, 24.6, 20.9; mass spectrum (70 eV) m/e 210, 208 (M$^+$, not observed), 150, 148 (M$^+$ - HOAc, 14.5, 14.9), 73 (8.0) 69 (66.0), 68 (13.9), 67 (6.1), 61 (23.6), 55 (9.6), 43 (100.0); high resolution mass spectrum (70 eV) m/e 149.9868, 147.9888 (calculated 149.9868, 147.9888 for C$_5$H$_9$Br).

5-Bromo-1-pentanol (Compound XXXI)

5-Bromopentanol-1-acetate (Compound XXXII) was hydrolyzed as described for the chloride. Fractional distillation of the crude product gave 5-bromo-1-pentanol (Compound XXXI) as a colorless oil (84%): bp 60°–70° C. (0.4 mm) (lit. Meyers et al. Tetrahedron 27, 5979–85 (1971) 62° C. (0.5 mm)); IR (film) cm$^{-1}$ 3340 (broad), 2940, 2875, 1460, 1440, 1380, 1275, 1250, 1230, 1205, 1140, 1060, 1020, 990, 955, 890, 740, 645; $^1$H NMR (200 MHz, CDCl$_3$) δ 3.68 (t, 6.2 Hz, 2H), 3.43 (t, 6.8 Hz, 2H), 2.38 (s, 1H), 1.90 (pentet, 7 Hz, 2H), 1.57 (m, 4H); $^{13}$C NMR (22.5 MHz, CDCl$_3$) δ 62.3, 33.8, 32.5, 31.5, 24.5; mass spectrum (70 eV) m/e (% base) 168, 166 (M$^+$, not observed), 150, 148 (M$^+$ - H$_2$O, 1.6, 1.6), 137, 135 (M$^+$ - .CH$_2$OH, 7.8, 8.0), 82 (5.2), 80 (5.2), 69 (100.0), 68 (14.4), 67 (5.9), 57 (13.0), 56 (13.0), 55 (30.1); high resolution mass spectrum (70 eV) m/e 136.9783, 134.9809 (calculated 136.9789, 134.9809 for C$_4$H$_8$Br).

5-Chloro-1-pentanol

The procedure reported by Meyers et al. Tetrahedron 27, 5979–85 was used. 5-Chloropentanol-1-acetate (33.9 g, 0.21 mole) was combined with EtOH (95%, 75 mL) and aqueous NaOH (2N, 90 mL) and shook until homogeneous. The solution was allowed to stand at room temperature for several hours, and the EtOH was removed in vacuum. The residue was extracted with OEt$_2$ (3×150 mL). After the extract was dried (K$_2$CO$_3$), it was stripped of solvent in vacuum and distilled, giving 5-chloro-1-pentanol as a colorless oil (21.1 g, 84%, lit.[119] 72%) bp 35°–7° C. (0.02 mm) (lit.[119] 62° C. (0.5 mm)); IR (film) cm$^{-1}$ 3330 (broad), 2945, 2875, 1455, 1440, 1315, 1295, 1265, 1150, 1075, 1060, 1020, 1000, 965, 900, 740, 725, 655; $^1$H NMR (200 MHz, CDCl$_3$) δ 3.67 (m, 2H), 3.55 (t, 6.5 Hz, 2H), 1.82 (pentet, 7 Hz, 2H), 1.4–1.7 (m, 4H), 1.37 (m, 1H); $^{13}$C NMR (22.5 MHz, CDCl3) δ 62.4, 45.0, 32.4, 31.9, 23.2; mass spectrum (70 eV) m/e (% base) 124, 122 (M$^+$, not observed), 106, 104 (M$^+$ - H$_2$O, 0.7, 1.3), 105 (0.5), 93 (7.1), 91 (20.5), 69 (13.7), 68 (100.0), 67 (13.6), 57 (13.4), 56 (41.4), 55 (57.0).

[(5-Chloro-1-pentyl)oxy](1,1-dimethylethyl)dimethylsilane

A mixture of t-butyldimethylsilyl chloride (29.5 g, 0.196 mole) and 5-chloro-1-pentanol (20 g, 0.163 mole) under an inert atmosphere was treated with a solution of imidazole (27.7 g, 0.407 mole) in dry DMF (40 mL). The reaction was stirred overnight at room temperature then partitioned between water (200 mL) and OEt$_2$ (300 mL). The aqueous layer was extracted with more OEt$_2$ (2×100 mL), and the combined extract was dried (Na$_2$SO$_4$). The OEt$_2$ was removed and the residue fractionally distilled. A small fore-run was collected (bp 57° C. (16 mm)) and then [(5-chloro-1-pentyl)oxy](1,1-dimethylethyl)dimethylsilane as a colorless oil (44.8 g, 97%): bp 120°-5° C. (17 mm), IR (film) cm$^{-1}$ 2960, 2940, 2900, 2865, 1475, 1465, 1390, 1365, 1290, 1260, 1110, 1055, 1030, 1010, 982, 940, 910, 840, 815, 780, 725, 660; $^1$H NMR (200 MHz, CDCl$_3$) δ 3.62 (t, 6.1 Hz, 2H), 3.54 (t, 6.7 Hz, 2H), 1.79 (pentet, 7 Hz, 2H), 1.52 (m, 4H), 0.89 (s, 9H), 0.05 (s, 6H); $^{13}$C NMR (22.5 MHz, CDCl$_3$) δ 62.8, 44.9, 32.5, 32.1, 26.0 (3C), 23.3, 18.3 (tertiary), −5.3 (2C); mass spectrum (70 eV) m/e (% base) 238, 236 (M$^+$, not observed), 181, 179 (M$^+$ - t-Bu., 1.0, 2.7), 125 (10.4), 123 (28.3), 95 (9.0), 93 (20.3), 75 (10.6), 73 (10.3) 70 (7.6), 69 (100.0); high resolution mass spectrum (70 eV) m/e 181.0636, 179.0656 (calculated 181.0630, 179.0660 for C$_7$H$_{16}$OClSi).

exo-6-Acetoxybicyclo[3.3.0]octan-3-one (Compound XV) from ethyl 3-oxotricyclo[3.3.0$^{2,8}$]octan-2-carboxylate (Compound XIV)

A solution of ethyl 3-oxotricyclo[3.3.0.0$^{2,8}$]octan-2-ylcarboxylate (Compound XIV, 9.4 g, 0.10 mole) and H$_2$SO$_4$ (0.5 mL) in HOAc (200 mL) was stirred and heated to 100° C. for 4 hours. The reaction was cooled, concentrated in vacuum, diluted with OEt$_2$ (400 ml), washed (sat. NaHCO$_3$ until no more CO$_2$ evolution; brine), dried (Na$_2$SO$_4$), and concentrated in vacuum once more. The yellow oil (13.7 g) was chromatographed (300 g silica gel; 4:1 (v/v) hexane-OEt$_2$, gradient to 1:1) giving four bands. The third band was distilled giving exo-6-acetoxybicyclo[3.3.0]ootan-3-one (Compound XV, 10.6 g, 58%) as a colorless oil: bp 90° C. (0.25 mm); IR (film) cm$^{-1}$ 2950, 2870, 1745, 1740, 1445, 1410, 1380, 1365, 1250, 1190, 1155, 1025, 990, 965, 950, 905, 870, 800; $^1$H NMR (200 MHz, CDCl$_3$) δ 4.94 (m, 1H), 1.3-3.1 (complex), 2.04 (s); $^{13}$C NMR (22.5 MHz, CDCl$_3$) δ 218.6, 170 5, 81.8, 46.1, 44.5, 41.7, 38.0, 31.3, 29.1, 27.1; mass spectrum (70 eV) m/e (% base) 182 (M$^+$, 0.3), 1.22 (38.8), 96 (7.9), 95 (7.2), 94 (7.2), 93 (22.3), 83 (10.2), 81 (14.0), 80 (100.0), 79 (15.3), 78 (9.9), 55 (5.8); high resolution mass spectrum (70 eV) m/e 182.0951 (calculated 182.0943 for C$_{10}$H$_{14}$O$_3$), 122.0733 (M$^+$ - HOAc, calculated 122.0732 for C$_8$H$_{10}$O); TLC (OEt$_2$, vanillin dip) R$_f$=0.47.

exo-2-Acetoxyspiro[bicyclo[3.3.01octan-7,2'[1,3]dioxolane1(Compound XVI)

A solution of 6-acetoxybicyclo[3.3.0]octan-3-one Compound XV, 10.0 g, 0.055 mole), ethylene glycol (50 mL), and p-toluenesulfonic acid (a few mg) in benzene (500 mL) was heated to reflux under a Dean-Stark trap until 1 equivalent of water was removed. After cooling to room temperature, the reaction was diluted with OEt$_2$, washed (sat. NaHCO$_3$; brine), dried (Na$_2$SO$_4$), and stripped of solvent in vacuum leaving a colorless oil (12.2 g, 98%), sufficiently pure for subsequent reactions. IR (film) cm$^{-1}$ 2965, 2880, 1740, 1460, 1440, 1380, 1365, 1340, 1250, 1210, 1125, 1105, 1025, 1000, 985, 950, 910, 870, 810, 735; $^1$H NMR (200 MHz, CDCl$_3$) δ 4.91 (m, 1H), 3.91 (s, 4H), 2.70 (m, 1H), 2.49 (rough quartet, 1H), 1.4-2.15 (complex), 2.02 (s, 3H); $^{13}$C NMR (22.5 MHz, CDCl$_3$) δ 170.6, 118.0, 81.9, 64.7, 64.0, 47.0, 41.5, 39.3, 38.7, 30.7, 30.3, 21.3; mass spectrum (70 eV) m/e (% base) 226 (M$^+$ not observed), 167 (M$^+$ - OAc, 40.4), 166 (M$^+$ - HOAc, 100.0), 139 (10.8), 125 (45.2), 112 (13.1), 99 (26.5), 87 (9.9), 86 (26.7), 81 (13.1), 80 (10.8), 79 (15.2), 55 (20.7); high resolution mass spectrum (70 eV) m/e 166.0994 (calculated 166.0994 for C$_{10}$H$_{14}$O$_2$); TLC (OEt$_2$, vinillin dip) R$_f$=0.50.

exo-2-Hydroxyspiro[bicyclo[3.3.0]octan-7,2'-[1,3 dioxolane] (Compound XVII)

exo-2-Acetoxyspiro[bicyclo[3.3.0]octan-7.2'-[1,3]dioxolane] (Compound XVI, 11.8 g, 0.052 mole) was stirred with ethanolic KOH (156 mL of 1N KOH in 95% EtOH, 0.156 mole) at room temperature for ¼ hour. The reaction was poured into water (500 mL) and extracted with OEt$_2$ (6×). The extract was dried (Na$_2$SO$_4$) and concentrated in vacuum to leave the title compound (Compound XVII, 8.52 g, 89%) as a white solid, sufficiently pure for subsequent reactions. Mp 54°-5.5° C.; IR (KBr) cm$^{-1}$ 3270 (broad), 2950, 2875, 1460, 1450, 1435, 1350, 1330, 1310, 1240, 1205, 1180, 1120, 1100, 1040, 1000, 985, 945, 900, 870, 835, 800, 720, 650, 590, 530, 470; $^1$H NMR (200 MHz, CDCl$_3$) δ 4.04 (m, 1H), 4.00 (s, 4H), 2.72 (m, 1H), 2.38 (rough quartet, 1H), 1.3-2.1 (complex, 8H); $^{13}$C NMR (22.5 MHz, CDCl$_3$) δ 118.4, 79.2, 64.6, 64.0, 49.5, 41.7, 39.4, 38.6, 33.6, 30.0; mass spectrum (70 eV) m/e (% base) 184 (M$^+$, 21.6), 139 (27.6), 126 (14.0), 125 (99.6), 99 (100.0), 96 (14.0), 86 (40.6), 83 (21.2), 81 (16.5), 79 (13.4), 67 (10.1), 57 (13.2), 55 (38.7), 53 (12.3); high resolution mass spectrum (70 eV) m/e 184.1097 (calculated 184.1100 for C$_{10}$H$_{16}$O$_3$); TLC (OEt$_2$, vanillin dip) R$_f$=0.25.

Pyridinium dichromate, PDC. PDC was prepared according to the procedure of Corey and Schmidt, Tet. Lett. 399-402 (1979) from CrO$_3$ and pyridine in water.

Spiro[bicyclo3.3.0]octan-7,2'-[1,3]dioxolane]2-one by PDC oxidation (Compound XIII)

2-Hydroxyspiro[bicyclo[3.3.0]octan-7,2'-[1.3]dioxolane] Compound XVIII, 0.50 g, 2.7 mmole) was added to a solution of PDC (7.15 g, 19 mmole) in DMF (50 mL) and stirred for 3 hours at room temperature. The reaction was poured into water (500 mL) and extracted with OEt$_2$ (3×). The extract was dried (Na$_2$SO$_4$) and concentrated in vacuum giving the title compound as a colorless oil (0.27 g, 55%): TLC (OEt$_2$, vanillin dip) R$_f$=0.40. IR (film) cm$^{-1}$ 2960, 2895, 1745, 1440, 1340, 1305, 1275, 1210, 1115, 1025, 1010, 955, 885, 810,; $^1$H NMR (200 MHz, CDCl$_3$) δ 3.89 (s, 4H), 2.91 (m, 1H), 2.61 (rough quartet, 1H), 2.0-2.55 (complex, 6H), 1.87 (m, 1H), 1.66 (d of d, 13.5, 6 Hz, 1H); $^{13}$C NMR (22.5 MHz, CDCl$_3$) δ 221.6, 117.5, 64.4, 64.3, 49.2, 41.6, 38.6, 37.2, 37.0, 26.4; high resolution mass spectrum (70 eV) m/e 182.0945 (calculated 182.0943 for C$_{10}$H$_{14}$O$_3$).

3-(5-Methoxy hept-1-en-yl)-cyclohexanone (Compound I) and 3-(5-hydroxyheptyl-1-ene)-cyclohexanone (Compound II)

The adduct of triphenyl phosphine and 1-bromo-5 methoxy heptane (9.5 g 21 m mole) in 15 ml of DMSO was added in toto to a cooled (zero degrees °C.) stirred solution of methyl sulfinyl methyl sodium (22 m mole in 10 ml of DMSO) under inert atmosphere. The reaction was allowed to warm to room temperature over a fifteen minute period 3-(acetyloxy) cyclohexanone (3.5 g 25 m mole was added at once and stirred for three days at room temperature. The material was hydrolized with dilute hydrochloric acid, and chromatographed on a 1.5×50 400 mesh silica gel column. The silica had been activated at 180° C., cooled in a desiccator. The column was packed in hexane, and eluted with a gradient of Et$_2$O and MeOH.

IR (film) cm$^{-1}$ 3450, 2950, 2865, 2840, 1705, 1645, 1630, 1475, 1350, 1335, 1260, 1205, 1130, 990, 930, 840 and IR (film) cm$^{-1}$ 3425, 2940, 2860, 2820, 1720, 1660, 1650, 1465, 1455, 1370, 1270, 1220, 1195, 1140, 980, 880 for the title compounds I and II respectively.

3-(5-Methoxy-pent-1-en-yl)-cyclohexanone (Compound III) and 3-(5-Hydroxy-pent-1-en-yl)-cyclohexanone (Compound IV)

The adduct of triphenyl phosphine and 1-bromo-5-methoxy pentane (Compound XXX, 9.0 g 21 m mole) in 15 ml of DMSO was added in toto to a cooled (zero degrees °C.) stirred solution of methyl sulfinyl methyl sodium (22 m mole in 10 ml of DMSO) under inert atmosphere. The reaction was allowed to warm to room temperature over a fifteen minute period. 3-(acetyloxy) cyclohexanone (3.5 g 25 m mole) was added at once and stirred for three days at room temperature. The material was hydrolyzed with aqueous hydrochloric acid, and chromatographed in the manner described above for Compounds I and II, to give the title compounds.

IR (film) cm$^{-1}$ 3450, 2945, 2865, 2840, 1705, 1640, 1625, 1470, 1370, 1340, 1260, 1195, 1190, 1135, 990, 925, 730, 670 and IR (film) cm$^{-1}$ 3425, 2950, 2865, 2840, 1700, 1680, 1640, 1625, 1465, 1365, 1330, 1265, 1225, 1190, 1170, 1130, 935, 725, 655, for Compounds III and IV, respectively.

3-(5-Methoxy hept-1-en-yl) cyclopentanone (Compound V) and 5-hydroxy-hept-1-en-yl) cyclopentanone (Compound VI)

Magnesium metal turnings (7.2 gm, 0.3 moles) were added to a three-neck, round bottom flask equipped with a Friedrich condenser and kept under nitrogen gas. Tetrahydrofuran (300 ml) was transferred to the flask and the contents allowed to stir. A clear, colorless solution of 1-chloro-5-methoxy-2-heptene (Compound XL, 48.1 gm, 0.3 moles) was added portionwise and refluxed. The final third portion was added and the mixture allowed to stir for three hours. The dark yellow solution was cooled to −70 degrees C., the condenser was removed and replaced with a dry ice addition funnel. A clear solution of 3-chlorocyclopentanone (35 gm, 03 moles) was added over one hour. The viscous solution was poured into two liters of acidic methanol and slowly warmed to room temperature. The products are chromatographed as described above for compounds I and II and the title compounds V and VI and other products are obtained. IR (film) cm$^{-1}$ 3435, 2950, 2905, 2810, 1730, 1660, 1620, 1475, 1440, 1420, 1380, 1370, 1180, 1138, 920, 735, 660 and IR (film) cm$^{-1}$ 3440, 2940, 2835, 2800, 1740, 1660, 1620, 1450, 1375, 1360, 1195, 1155, 1100, 910, 730, 665, for Compound V and VI respectively.

3-(5-Methoxy pent-1-en-yl) cyclopentanone (Compound VII) and 3-(5-hydroxy-pent-1-en-yl) cyclopentanone (Compound VIII)

Magnesium metal turnings (7.2 gm, 13 moles) were added to a three-neck, round bottom flask equipped with a Friedrich condenser and kept under nitrogen gas. Tetrahydrofuran (300 ml) was transferred to the flask and the contents allowed to stir. A clear, colorless solution of 1-chloro-5-methoxy-2-pentene (Compound L, 40 gm, 0.3 moles) was added portionwise and refluxed. The final third portion was added and the mixture allowed to stir for three hours. The dark yellow solution was cooled to −70 degrees C., the condenser was removed and replaced with a dry ice addition funnel. A clear solution of 3-chlorocyclopentanone (35 gm, 0.3 moles) was added over one hour. The viscous solution was poured into two liters of acidic methanol and slowly warmed to room temperature. The products are chromotographed in the manner described above for Compounds I and II, and the title compounds VII and VIII, and other are obtained.

IR (film) cm$^{-1}$ 3450, 2945, 2865, 2840, 1705, 1640, 1625, 1470, 1370, 1340, 1260, 1195, 1190, 1135, 990, 925, 730, 670 and 3425, 2950, 2865, 2840, 1700, 1680, 1640, 1625, 1465, 1365, 1330, 1265, 1225, 1190, 1170, 1130, 935, 725, 655, for Compounds VII and VIII, respectively.

5-[(1,1-Dimethylethyl)dimethylsiloxy]pent-1-ylmagnesium bromide

A mixture of Mg turnings (0.6 g, 24 mmole), [(5-bromo-1-pentyl)oxy]-(1,1-dimethylethyl)dimethylsilane (0.5 mL), and MeMgBr (0.2 mL, 3 M) in dry OEt$_2$ (5 mL) was stirred and heated to reflux for 5 minutes under an inert atmosphere. A solution of [(5-bromo-10-pentyl)oxy](1,1-dimethyl-ethyl)dimethylsilane (5.62 g, 20 mmole) and MeMgBr (0.2 mL, 3 M) in dry OEt$_2$ (20 mL) was added dropwise at a rate to maintain a gentle, unassisted reflux. After addition was complete, the reaction was heated at reflux for 45 minutes. The solution of Grignard reagent was then cooled and used immediately in the next reaction.

2-[5-[(1,1-Dimethylethyl)dimethylsiloxy]pent-1-yl]-2-hydroxyspiro-[bicyclo[3.3.0]octan-7,2'-[1,3]dioxolane]

A solution of spiro-[bicyclo[3.3.0]octan-7,2'-[1,3]dioxolane]-2-one (Compound XIII, 0.50 g, 2.7 mmole) in dry OEt$_2$ (20 mL) was added dropwise to a −78° C., stirred solution of 5-[(1,1-dimethylethyl)dimethylsiloxy]pent-1-ylmaqnesium bromide (14 mmole in 25 mL OEt$_2$) all under an inert atmosphere. The reaction was stirred ½ hour at −78° C. and 1 hour at room temperature. It was poured into sat. NaHCO$_3$ and extracted with OEt$_2$ (3×). The extract was dried (Na$_2$SO$_4$), stripped of solvent in vacuum, and chromatographed (80 g silica gel, eluted with 4:1 (v/v) hexane-OEt$_2$, gradient to 100% OEt$_2$) giving four bands. The first band was (1,1-dimethylethyl)dimethyl(pentyloxy)silane 2.21 g, 78% of starting bromide): identical to authentic material, TLC (OEt$_2$, vanillin dip) R$_f \approx$0.7, not visible.

The second band was the Grignard addition product, Compound LX in accordance with Formula 3, see Reaction Scheme 1, (0.77 g, 74%): IR (film) cm$^{-1}$ 3500 (broad), 2950, 2935, 2885, 2860, 1475, 1465, 1445, 1430, 1405, 1390, 1365, 1350, 1330, 1255, 1220, 1190, 1100, 1015, 995, 945, 895, 835, 815, 775, 710, 660; $^1$H NMR (200 MHz, CDCl$_3$) δ 3.93 (m, 4H), 3.60 (t, 6.4 Hz, 2H), 6.20 (s, 1H), 2.55 (m, 1H), 2.37 (t of d, 10, 2 Hz, 1H), 1.15–2.1 (complex, 16H), 1.90 (s, 9H), 0.04 (s, 6H); $^{13}$C NMR (22.5 MHz, CDCl$_3$) δ 119.2, 81.6, 64.4, 64.2, 63.3, 49.3 41.7, 41.0, 40.8, 40.5, 34.8, 32.9, 30.7, 26.5, 26.0 (3C), 24.4, (22.1), 18.4, −5.2 (2C); high resolution mass spectrum (70 eV) m/e 384.2722 (M$^+$, 1.2% of base, calculated 384.2697 for C$_{21}$H$_{40}$O$_4$Si), 327.1994 (M$^+$ - t-Bu., 98.4% of base, calculated 327.1992 for C$_{17}$H$_{31}$O$_4$Si); TLC (OEt$_2$, Vanillin dip) R$_f$=0.53.

The third band was a by-product due to the MeMgBr initiator, 2-hydroxy-2-methylspiro[bicyclo[3.3.0]octan-7,2'-[1,3]dioxolane](0.02 g): $^1$H NMR (60 MHz, CDCl$_3$) δ 3.95 (s, 4H), 3.2 (s, 1H), 1.1–2.8 (complex, 10H), 1.25 (s, 3H); TLC (OEt$_2$, vanillin dip) R$_f$ =0.29.

The fourth band was the ketone reduction product, 2-hydroxyspiro-[bicyclo[3.3.0]octan-7,2'-[1,3]dioxolane] (0.04 g): $^1$H NMR (60 MHz, CDCl$_3$) δ 4.15 (m, 1H), 3.95 (s, 4H), 1.2–3.1 (complex, 11H); TLC (OEt$_2$, vanillin dip) R$_f$=0.23.

Dehydration of 2-[5-[(1,1-dimethylethyl)dimethylsiloxy]pent-1-yl]-2-hydroxyspiro[bicyclo[3.3.0]octan-7,2'-[1,3]dioxolane] (Compound LX), with thionyl chloride in pyridine A stirred solution of 2-[5-[(1,1-dimethylethyl)dimethylsiloxy]pent-1-yl]-2-hydroxyspiro[bicyclo[3.3.0]-octan-7,2'-[1,3]dioxolane] (Compound LX 0.91 2.4 mmole) in dry pyridine (40 mL) under an inert atmosphere was cooled to −10° C. and treated dropwise with purified SOCl$_2$ (5 mL). After stirring ½ hour at −10° C., the reaction was cooled to −25° C., poured into ice water (250 mL water and 100 g ice), and extracted with OEt$_2$ (4×). The extract was dried (Na$_2$SO$_4$), stripped of solvent in vacuum, and chromatographed (80 g silica gel, eluted with 4:1 (v/v hexane-OEt$_2$) giving a mixture of olefins, in accordance with Formula 4 (Reaction Scheme 1) as a colorless oil (0.741 g, 85%): IR (film) cm$^{-1}$ 3040, 2955, 2935, 2885, 2860, 1650, 1475, 1465, 1435, 1390, 1360, 1330, 1255, 1215, 1105, 1045, 1025, 1005, 945, 840, 815, 780, 715, 665; $^1$H NMR (200 MHz, CDCl$_3$) δ 5.05–5.25 (m, <1H), 3.90 (m, 4H), 3.60 (t, 6.5 Hz, 2H), 1.1–3.1 (complex, ~16H), 0.89 (s, 9H), 0.05 (s, 6H); $^{13}$C NMR (22.5 MHz, CDCl$_3$) complex, major peaks are found at δ 146.6, 121.4, 121.3, 120.7, 118.6, 64.7, 64.6, 64.4, 63.9, 63.7, 63.2, 62.8, 62.2, 49.2, 46.0, 43.9, 42.7, 42.0, 41.8, 41.2, 41.0, 40.8, 39.0, 38.7, 38.3, 36.3, 32.7, 32.5, 32.3, 32.0, 31.0, 29.5, 29.3, 28.2, 27.7, 27.4, 26.0, 25.8, 22.2, 18.4, −5.2; high resolution mass spectrum (70 eV) m/e 366.2592 (M$^+$, calculated 366.2591 for C$_{21}$H$_{38}$O$_3$Si); TLC (OEt$_2$, vanillin dip) R$_f$=0.65.

Deprotection of olefin mixture in accordance with Formula 4

The mixture of isomers, (0.74 g, 2.0 mmole) was treated with a 5% solution of 48% aqueous HF in CH$_3$CH (35 mL) for 7 minutes at room temperature. The reaction was quenched with a mixture of sat. NaHCO$_3$ (50mL) and water (50 mL) and then extracted with CHCl$_3$ (100 mL; 2×50 mL). The extract was dried (Na$_2$SO$_4$), concentrated in vacuum, and chromatographed (80 g silica gel, eluted with 4:1 (v/v) hexane-OEt$_2$, gradient to 1:4) giving 3 bands. The first band was 6-(5-hydroxypent-1-yl)bicyclo[3.3.0]oct-5-en-3-one: (64 mg, 15%): IR (film) cm$^{-1}$ 3400 (broad), 2930, 2860, 1748,, 1460, 1440, 1395, 1325, 1275, 1250, 1225, 1190, 1130, 1075, 1060, 1020: $^1$H NMR (200 MHz, CDCl$_3$) δ 3.64 (rough q, 2H), 3.12 (m, 1H), 2.90 (d, 21 Hz, 1H), 2.67 (d, 21 Hz, 1H), 2.62 (d of d, 18, 8.5 Hz, 1H), 2.57 (m, 1H), 2.32 (m, 2H), 2.09 (rough t, 7 Hz, 2H), 1.88 (d of d, 18, 10.5, 1H), 1.1–1.7 (complex, 7H): $^{13}$C NMR (22.5 MHz, CDCl$_3$) δ 218.7, 136.2, 135.3, 62.8, 48.0, 47.4, 38.9, 37.6, 33.0, 32.6, 29.5, 27.7, 25.7; TLC (OEt$_2$, vanillin dip) R$_f$=0.30. This first band material partially isomerized over 2 days of standing to the 4 position olefin. $^1$NMR (200 MHz, CDCl$_3$) showed new peaks at δ 6.13, 6.05 and 1.1–3.3 (complex); IR (film) showed new peaks at 1700 and 1630 cm$^{-1}$; UV (95% EtOH) nm,292, 229 ($\epsilon_{223/9}/\epsilon_{292}$=12); TLC (OEt$_2$, vanillin dip) R$_f$=0.32, 0.12.

Band 2 was a mixture of 3 olefins. It was mostly 6-(5-hydroxypent-1-yl)bicyclo[3.3.0]oct-6-en-3-one, and to a lesser extent the Z and E isomers of the title compound, Compound X, namely 6-(5-hydroxypent-1-en-yl)bicyclo[3.3.0]octan-3-one (0.275 g):

The mixture of olefins was chromatographed, as described for compounds I and II to yield the title compound X, IR (film). 3440, 2860, 1745, 1472, 1410, 1250, 1175, 1060, 735, 660: Yield 2–3%. The IR spectrum of the title compounds IX is: 3444, 2860, 1742, 1405, 1252, 1175, 1070, 740, 665.

Compound XI and XII can be obtained by a procedure analogous to the procedure for obtaining compounds IX and X.

Compound XI IR (film) cm$^{-1}$ 2928, 2940, 2864, 1744, 1472, 1459, 1402, 1252, 1160, 1070, 730, 635.

Compound XII IR (film) cm$^{-1}$ 3428, 2944, 2858, 1738, 1765, 1468, 1409, 1245, 1165, 1065, 728, 635.

What is claimed is:

1. A compound selected from the group consisting of compounds of the formula (i), (ii) and (iii),

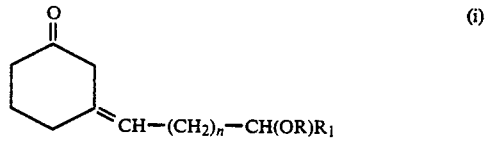
(i)

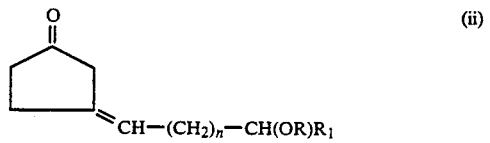
(ii)

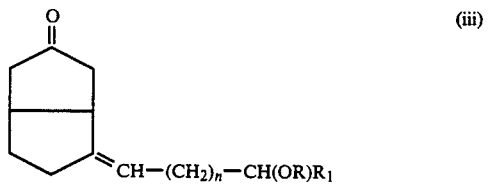
(iii)

where
R is H, alkyl of 1 to 6 carbons, or CO—R$_2$ where R$_2$ is alkyl of 1 to 6 carbons;
R$_1$ is H, CH$_3$, or (CH$_2$)$_m$—CH$_3$;
n is an integer having the values of 2 to 10, and
m is an integer having the values of 1 to 6.

2. A compound in accordance with claim 1 which has the formula (i).

3. A compound in accordance with claim 2 wherein n is 3, and R$_1$ is H.

4. A compound in accordance With claim 3 wherein R is H.

5. A compound in accordance with claim 3 wherein R is OCH$_3$.

6. A compound in accordance with claim 2 wherein n is 3, and R$_1$ is CH$_2$CH$_3$.

7. A compound in accordance with claim 6 wherein R is H.

8. A compound in accordance with claim 6 wherein R is OCH$_3$.

9. A compound in accordance with claim 2 wherein R is CO—R$_2$.

10. A compound in accordance with claim 1 which has the formula (ii).

11. A compound in accordance with claim 10 wherein n is 3, and R$_1$ is H.

12. A compound in accordance with claim 11 wherein R is H.

13. A compound in accordance with claim 11 wherein R is OCH$_3$.

14. A compound in accordance with claim 10 wherein n is 3, and R$_1$ is CH$_2$CH$_3$.

15. A compound in accordance with claim 14 wherein R is H.

16. A compound in accordance with claim 14 wherein R is OCH$_3$.

17. A compound in accordance with claim 10 wherein R is CO—R$_2$.

18. A compound in accordance with claim 1 which has the formula (iii).

19. A compound in accordance with claim 18 wherein n is 3, and R$_1$ is H.

20. A compound in accordance with claim 19 wherein R is H.

21. A compound in accordance with claim 19 wherein R is OCH$_3$.

22. A compound in accordance with claim 18 wherein n is 3, and R$_1$ is CH$_2$CH$_3$.

23. A compound in accordance with claim 22 wherein R is H.

24. A compound in accordance with claim 22 wherein R is OCH$_3$.

25. A compound in accordance with claim 18 wherein R is CO—R$_2$.

26. A method of blocking androgen receptor sites in a mammal which comprises administering to said mammal a pharmaceutical composition which contains an effective dose of a compound which is selected from a group consisting of compounds of the formula (i), (ii) and (iii),

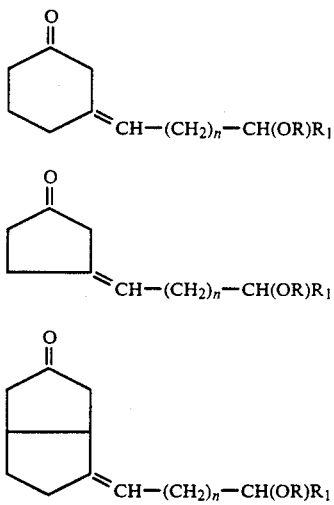

where
R is H, alkyl of 1 to 6 carbons, or CO—R$_2$ where R$_2$ is alkyl of 1 to 6 carbons;
R$_1$ is H, CH$_3$, or (CH$_2$)$_m$—CH$_3$;
n is an integer having the values of 2 to 10, and
m is an integer having the values of 1 to 6.

27. The method of claim 26 wherein the pharmaceutical composition is adapted for topical administration and is applied topically.

28. The method of claim 26 wherein the pharmaceutical composition is adapted for internal administration and is administered internally.

29. The method of claim 26 wherein the pharmaceutical composition is administered to a mammal afflicted with acne.

30. The method of claim 26 wherein the pharmaceutical composition is administered to a human afflicted with male pattern baldness.

31. The method of claim 26 wherein the pharmaceutical composition is administered to a mammal afflicted with keloids.

32. The method of claim 26 wherein the pharmaceutical composition is administered to a mammal for the purpose of promoting synthesis of elastin.

33. The method of claim 26 wherein the pharmaceutical composition is administered to a human female who has a foreign body mammary insert, for the purpose of decreasing fibroblast capsules formed around the insert.

34. The method of claim 26 wherein the pharmaceutical composition is administered topically for the purpose of treating wrinkled skin of a human.

35. The method of claim 26 wherein the pharmaceutical composition is administered to a human afflicted with Alzheimer's disease.

36. The method of claim 26 wherein the pharmaceutical composition is administered to a human afflicted with a yeast infection.

37. The method of claim 26 wherein the pharmaceutical composition is administered to a human afflicted with osteoarthritis.

38. A method of controlling the growth of a microrganism or fungus which has androgen receptor sites, wherein blocking of said androgen receptor sites controls the growth of the microorganism or fungus, the method comprising the step of administering to said microrganism or fungus a pharmaceutical composition comprising an effective dose of of a compound of the formula (i), (ii) and (iii),

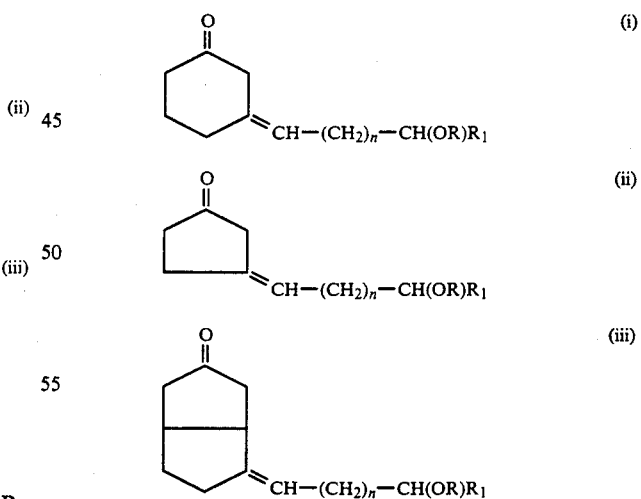

where
R is H, alkyl of 1 to 6 carbons, or CO—R$_2$ where R$_2$ is alkyl of 1 to 6 carbons;
R$_1$ is H, CH$_3$, or (CH$_2$)$_m$—CH$_3$;
n is an integer having the values of 2 to 10, and
m is an integer having the values of 1 to 6.

* * * * *

UNITED STATES PATENT AND TRADEMARK OFFICE
CERTIFICATE OF CORRECTION

PATENT NO. : 5,264,619

DATED : November 23, 1993

INVENTOR(S) : Larry C. Ford

It is certified that error appears in the above-identified patent and that said Letters Patent is hereby corrected as shown below:

Column 6, in the Reaction Scheme 2, between compounds XV and XVI, "H$^{\circ}$" should be --H$^{+}$--;

Column 6, line 66-67, "X and XX" should be --I and II--;

Column 10, line 47, "81:" should be --51:--;

Column 12, line 64, insert a heading --Biological Assays - Keloids and Capsules--;

Column 13, line 33, insert the following:

--Percent of excess (non-essential) androgen receptor blocked.

| Compound #I | Compound #II | Compund #V | Compound #X |
|---|---|---|---|

--;

Column 16, line 66, "CH$_3$CH$_2$" should be --CH$_3$.--;

Column 17, line 24, "3);" should be --3H);--;

Column 18, line 62, after "OEt$_2$" delete "1";

Column 19, line 29, "ootan" should be --octan--;

Column 19, line 35, "170 5" should be --170.5--;

Column 19, line 44, "[3.3.01]" should be --[3.3.0[--;

Column 19, line 45, "dioxolanel" should be --dioxolane]--;

Column 20, line 34, before "Compound" insert --(--.

UNITED STATES PATENT AND TRADEMARK OFFICE
CERTIFICATE OF CORRECTION

PATENT NO. : 5,264,619

DATED : November 23, 1993

INVENTOR(S) : Larry C. Ford

It is certified that error appears in the above-identified patent and that said Letters Patent is hereby corrected as shown below:

Column 2, line 35, "microrganisms" should be --microorganisms--;

Column 9, lines 29-30, "between balding, frontal tissues and hair bearing," should be --of balding, frontal tissues and of hair bearing,--;

Column 14, line 55, "Cl" should be --CL--;

Column 15, line 25, after "speaking" insert --,--;

Column 16, line 44, after "3H)." delete ")";

Column 21, line 43, "03" should be --0.3--.

Signed and Sealed this

Sixteenth Day of August, 1994

BRUCE LEHMAN

Attest:

*Attesting Officer*  *Commissioner of Patents and Trademarks*

UNITED STATES PATENT AND TRADEMARK OFFICE
CERTIFICATE OF CORRECTION

PATENT NO. : B1-5,264,619
DATED : May 14, 1996
INVENTOR(S) : Ford

It is certified that error appears in the above-indentified patent and that said Letters Patent is hereby corrected as shown below:

Title page, item [57], line 5 from the bottom, "symtoms" should be
--symptoms--;

Signed and Sealed this

Twenty-first Day of January, 1997

Attest:

BRUCE LEHMAN

*Attesting Officer*       *Commissioner of Patents and Trademarks*

REEXAMINATION CERTIFICATE (2883rd)

United States Patent [19]

Ford

[11] B1 5,264,619
[45] Certificate Issued May 14, 1996

[54] ANTI-ANDROGENIC CYCLO AND BICYCLO ALKENES

[75] Inventor: Larry C. Ford, Irvine, Calif.

[73] Assignee: Cosmos Pharmaceutical Corporation, Newport Beach, Calif.

Reexamination Request:
No. 90/003,955, Sep. 12, 1995

Reexamination Certificate for:
Patent No.: 5,264,619
Issued: Nov. 23, 1993
Appl. No.: 4,972
Filed: Jan. 15, 1993

[51] Int. Cl.⁶ ............... C07C 67/02; A61K 31/12; A61K 31/22
[52] U.S. Cl. ............... 560/256; 514/546; 514/691; 514/729
[58] Field of Search ............... 560/256; 514/546, 514/691, 729

[56] References Cited

U.S. PATENT DOCUMENTS 4,689,345  8/1987  Kasha et al. ............... 514/546

*Primary Examiner*—José G. Dees

[57] ABSTRACT

Compounds having the formula (i), (ii) and (iii),

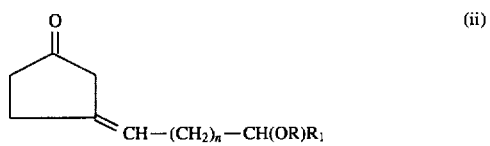
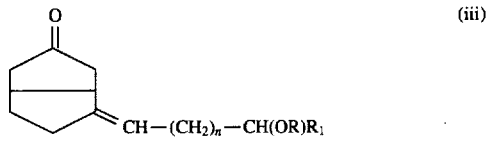

where R is H, alkyl of 1 to 6 carbons, or $CO-R_2$ where $R_2$ is alkyl of 1 to 6 carbons; $R_1$ is H, $CH_3$, or $(CH_2)_m-CH_3$; n is an integer having the values of 2 to 10, m is an integer having the values of 1 to 6, have anti-androgen activity on secondary androgen receptor sites. The compounds are useful for treating mammals, including humans afflicted with acne, male pattern baldness, adhesions and keloids. The compounds are also effective for treating other diseases or conditions which are related to androgen receptors, such as undesirable formation of breast capsules in females after breast augmentation surgery, osteoarthritis and symtoms of Alzheimer's disease. The compounds also have inhibitory effect on the metabolism of certain microorganisms and fungi of the kind, the metabolism of which is normally known to be controllable by anti-androgen compounds.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 26–38 is confirmed.

Claims 18–25 are cancelled.

Claims 1, 5, 8, 13 and 16 are determined to be patentable as amended.

Claims 2–4, 6, 7, 9–12, 14, 15 and 17, dependent on an amended claim, are determined to be patentable.

1. A compound selected from the group consisting of compounds of the formula (i)[,] *and* (ii) [and (iii)],

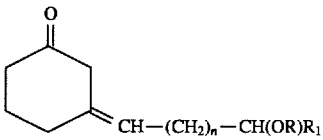

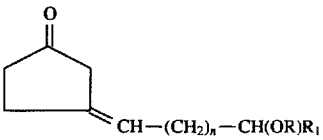

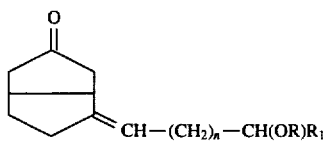

where

R is H, alkyl of 1 to 6 carbons, or CO—$R_2$ where $R_2$ is alkyl of 1 to 6 carbons;

$R_1$ is H, CH $CH_3$, or $(CH_2)_m$—$CH_3$;

n is an integer having the values of 2 to 10, and m is an integer having the values of 1 to 6.

5. A compound in accordance with claim 3 wherein R is [$OCH_3$] *$CH_3$*.

8. A compound in accordance with claim 6 wherein R is [$OCH_3$] *$CH_3$*.

13. A compound in accordance with claim 11 wherein R is [$OCH_3$] *$CH_3$*.

16. A compound in accordance with claim 14 wherein R is [$OCH_3$] *$CH_3$*.

* * * * *